(12) United States Patent
Sumiyoshi

(10) Patent No.: US 6,385,215 B1
(45) Date of Patent: May 7, 2002

(54) LASER OSCILLATION METHOD AND DEVICE AND LASER SCALPEL

(75) Inventor: Tetsumi Sumiyoshi, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/346,398

(22) Filed: Jul. 1, 1999

(30) Foreign Application Priority Data

Jul. 1, 1998 (JP) .......................................... 10-186217

(51) Int. Cl.$^7$ ................................................ H01S 3/30
(52) U.S. Cl. ............................ 372/6; 372/700; 372/27; 372/102; 372/64; 372/12; 372/20; 372/26; 372/28; 372/31; 372/32
(58) Field of Search ............................... 372/700, 6, 27, 372/102, 64, 12, 20, 28, 26, 31, 32; 385/11, 37; 359/341

(56) References Cited

U.S. PATENT DOCUMENTS

| | | | |
|---|---|---|---|
| 4,680,767 A | * 7/1987 | Hakimi et al. ................. | 372/6 |
| 4,964,131 A | * 10/1990 | Liu et al. ....................... | 372/6 |
| 5,191,586 A | * 3/1993 | Huber ............................ | 372/6 |
| 5,237,576 A | * 8/1993 | DiGiovanni et al. ........... | 372/6 |
| 5,432,806 A | * 7/1995 | Snitzer .......................... | 372/6 |
| 5,461,687 A | * 10/1995 | Brock ........................... | 372/700 |
| 5,511,083 A | * 4/1996 | D'Amato et al. .............. | 372/6 |
| 5,546,481 A | * 8/1996 | Meltz et al. ................... | 385/11 |
| 5,930,030 A | * 7/1999 | Scifres ........................... | 359/341 |

FOREIGN PATENT DOCUMENTS

| | | |
|---|---|---|
| JP | 2-52475 | 2/1990 |
| JP | 5-226737 | 9/1993 |
| JP | 5-343768 | 12/1993 |
| JP | 8-97491 | 4/1996 |
| JP | 9-162740 | 5/1997 |
| JP | 10-335734 | 12/1998 |

OTHER PUBLICATIONS

T. Sumiyoshi et al., "Dual wavelength (3 μm and 2 μm) CW cascade oscillation of a holmium–doped clad fiber laser", Conf. Proc. Int. LEOS '97 10$^{th}$ Annual Meet. 1997, vol. 2, pp. 534–535.

* cited by examiner

*Primary Examiner*—Leon Scott, Jr.
(74) *Attorney, Agent, or Firm*—Young & Thompson

(57) ABSTRACT

A laser oscillation device, which has an optical fiber where laser ion is doped; an excitation emission element that generates one laser beam including multiple wavelength components by exciting the laser ion in the optical fiber by light emission; a total reflection element that is located at one end of the optical fiber and reflects uniformly laser beam with multiple wavelengths; a separation optical element that is located at another end of the optical fiber and separates laser beam into beams with multiple wavelengths; and a plurality of partial reflection element that reflect separately laser beams with multiple wavelengths separated by the separation optical element.

35 Claims, 5 Drawing Sheets

LASER OSCILLATION METHOD AND DEVICE AND LASER SCALPEL

FIELD OF THE INVENTION

This invention relates to a laser oscillation method and device for emitting laser beam with multiple wavelengths using optical fiber as a gain medium, and relates to a laser scalpel using such a laser oscillation device.

BACKGROUND OF THE INVENTION

Currently, laser oscillation devices to emit laser beam have been used for various apparatuses. For example, a laser scalpel equipped with a gas laser tube as a laser oscillation device is also put to practical use. While other than the gas laser tube a semiconductor laser is widely used as a laser oscillation device, typical laser oscillation devices emit a single wavelength of laser beam.

However, for the laser scalpel it is requested that laser beam with multiple wavelengths can be emitted according to various uses. As a laser oscillation device to comply with this request, there is a fiber laser. In this fiber laser, an optical fiber that laser ion is doped functions as a gain medium, and laser beam with multiple wavelengths can be emitted by cascade oscillation.

FIG. 1 shows the entire structure of fiber laser. Referring to FIG. 1, the fiber laser as a conventional laser oscillation device is explained below. In a fiber laser 1 illustrated herein, reflection elements 3, 4 each are disposed at both sides of an optical fiber 2 as the gain medium, and a light emitting element 5 as excitation emission means opposes to one reflection element 3.

The optical fiber 2 is of glass fiber, into the core of which given laser ion is doped. The light emitting element 5 is, for example, composed of LD (laser diode) whose emission makes laser ion of the optical fiber 2 excite to generate one laser beam including multiple wavelength components.

The one reflection element 3 to which the light emission 5 opposes is, for example, composed of a dichroic mirror, which efficiently transmits light beam with excitation wavelength generated by the light emitting element 5 but efficiently reflects light beam with oscillation wavelength resonated by the optical fiber 2. The other reflection element 4 is, for example, composed of a half mirror (semitransparent mirror), which reflects and transmits laser beam excited by the optical fiber 2 according to its intensity.

In the fiber laser 1 described above, when emission of the light emitting element 5 is led through the reflection element 3 to the optical fiber 2, laser ion of the optical fiber 2 is excited to generate laser beam with multiple wavelengths. The laser beam is resonated between a pair of the reflection elements 3 and 4, emitted outside from the reflection element 4 at a given intensity.

Since laser beam thus emitted has multiple wavelength components, they are available to various apparatuses that need this property. However, the intensity ratio of multiple wavelengths in laser beam may not be in a desired condition. In this case, the intensity of a specific wavelength component needs to be reduced.

For example, as shown in FIG. 1, by using an optical filter 6 that gives a specific transmissivity to a specific wavelength, the intensity ratio of multiple wavelengths in laser beam eat be corrected into a desired condition. Further, by selecting one of optical filters 6 with various properties, the intensity ratio of multiple wavelengths in laser beam can be varied arbitrarily.

Also, like a fiber laser 11 in FIG. 2 laser beam can be reflected in different directions for each of multiple wavelengths by a wavelength dispersion element 12 such as a diffraction grating and a prism, and its intensity can be separately modulated by multiple optical filters 13, 14.

As described above, the fiber lasers 1, 11 can emit laser beam with multiple wavelengths, and the intensity ratio of multiple wavelengths can be brought into a desired condition. However, in case of the first fiber laser 1, for laser beam with three or more wavelengths, it is difficult to bring the intensity ratio into a desired condition. Also, it is difficult to change the intensity of a specific wavelength component in a continuous and dynamic a manner.

In case of the second fiber laser 11, even for laser beam with three or more wavelengths, the intensity ratio can be brought into a desired condition. However, it is still difficult to change the intensity of a specific wavelength component in a continuous and dynamic manner. Further, since it is difficult to multiplex multiple laser beams separated for respective wavelengths into one beam, it is not suitable for an apparatus having such a requirement.

Further, both the first and second fiber lasers 1, 11 resonate laser beam generated at the optical fiber 2 while reflecting it by the reflection elements 3, 4 on both sides. In this laser resonance, an optimum reflection factor has to be differentiated to each of the multiple wavelengths. However, in the fiber lasers 1, 11, multiple wavelength components of one laser beam are reflected uniformly by one reflection element 3 or 4 at each side of the optical fiber 2. Therefore, the operation of laser resonance cannot reach the optimum condition.

SUMMARY OF THE INVENTION

Accordingly, it is an object of the invention to provide a laser oscillation method that one laser beam including multiple wavelengths can be generated in the optimum condition and the intensity of multiple wavelengths can be modulated separately.

It is a further object of the invention to provide a laser oscillation device that one laser beam including multiple wavelengths can be generated in the optimum condition and the intensity of multiple wavelengths can be modulated separately.

It is a still further object of the invention to provide a laser scalpel using such a laser oscillation device.

According to the invention, a laser oscillation method for generating one laser beam including multiple wavelength components by locating reflection means for reflecting laser beam at both ends of an optical fiber where laser ion in doped and by exciting the laser ion in the optical fiber by light emitted from an excitation emission means, comprises the step of:

separating laser beam emitted from at least one end of the optical fiber into beams with multiple wavelengths; and
   reflecting separately the beams with multiple wavelengths by the reflection means.

According to another aspect of the invention, a laser oscillation device for generating one laser beam including multiple wavelength components by locating reflection means for reflecting laser beam at both ends of an optical fiber where laser ion is doped and by exciting the laser ion in the optical fiber by light emitted from an excitation emission means, comprises:

a separation optical means that is located at least at one end of the optical fiber and separates laser beam into beams with multiple wavelengths;

wherein the beams with multiple wavelengths separated by the separation optical means are reflected separately by the reflection means.

According to another aspect of the invention, a laser oscillation device, comprises:

an optical fiber where laser ion is doped;

an excitation emission means that generates one laser beam including multiple wavelength components by exciting the laser ion in the optical fiber by light emission;

a total reflection means that is located at one end of the optical fiber and reflects uniformly laser beam with multiple wavelengths;

a separation optical means that is located at another end of the optical fiber and separates laser beam into beams with multiple wavelengths; and a plurality of partial reflection means that reflect separately laser beams with multiple wavelengths separated by the separation optical means.

According to another aspect of the invention, a laser oscillation device, comprises:

an optical fiber where laser ion is doped;

an excitation emission means that generates one laser beam including multiple wavelength components by exciting the laser ion in the optical fiber by light emission;

a pair of separation optical means that are located individually at both ends of the optical fiber and separates laser beam into beams with multiple wavelength; and a plurality of partial reflection means that reflect separately laser beams with multiple wavelengths separated by the separation optical means.

According to another aspect of the invention, a laser scalpel, comprises:

the laser oscillation device defined above;

a laser leading means that leads laser beam output from the laser oscillation device to its tip portion movable; and an imaging optical means that is located near the tip portion of the laser leading means and converges laser beam to transmit through.

Meanwhile, the various means mentioned in this invention may be formed to realize their functions. For example, they may include a dedicated hardware, a computer that a proper function is applied through a program, a function given inside a computer through a proper program and a combination of these.

Also, the various means mentioned in this invention do not need to be formed as separate parts and may be part of another means. For example, a reflection means for reflecting laser beam at the end of optical fiber can be junctioned to the end face of optical fiber as a dedicated reflection element. However, it is also possible to use the end face of optical fiber as a reflection means.

BRIEF DESCRIPTION OF THE DRAWINGS

The invention will be explained in more detail in conjunction with the appended drawings, wherein.

DESCRIPTION OF THE PREFERRED EMBODIMENTS

Figure 1:
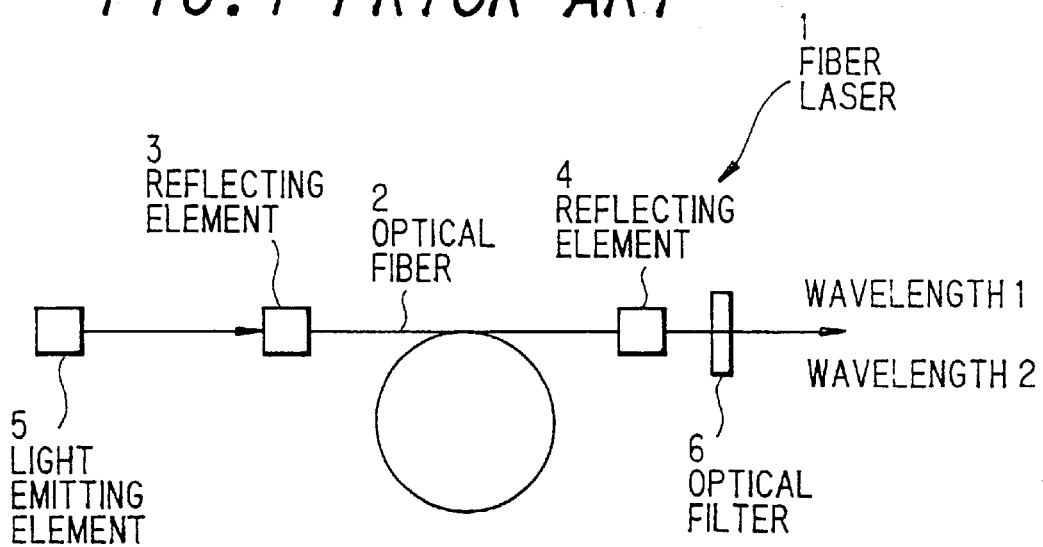
FIG. 1 is an illustration showing the first conventional laser oscillation device.
Figure 2:
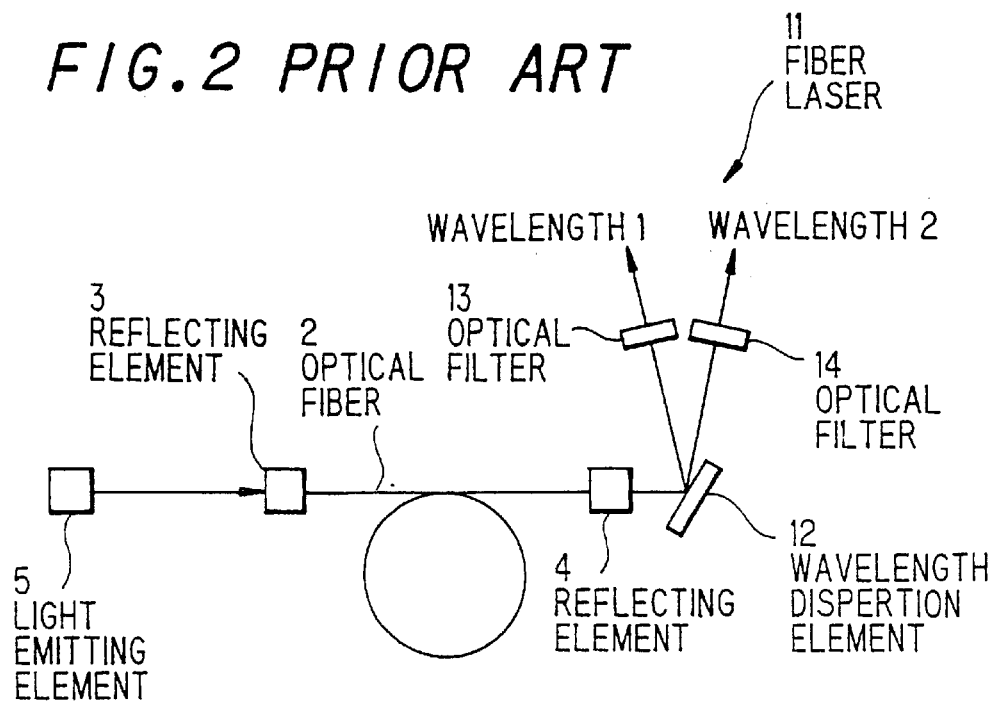
FIG. 2 is an illustration showing the second conventional laser oscillation device.
Figure 3:
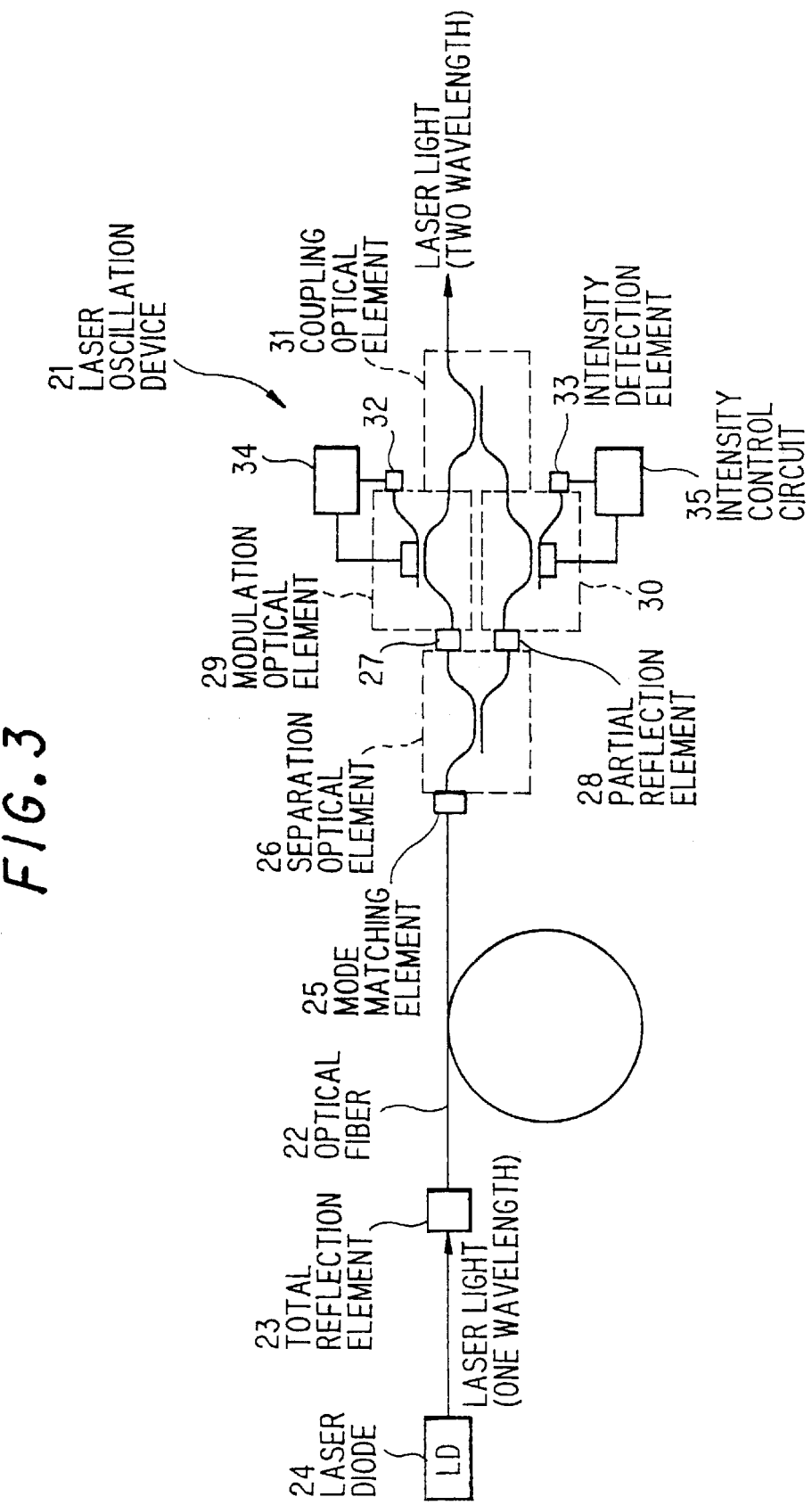
FIG. 3 is an illustration showing a laser oscillation device in a preferred embodiment according to the invention.
Figure 4:
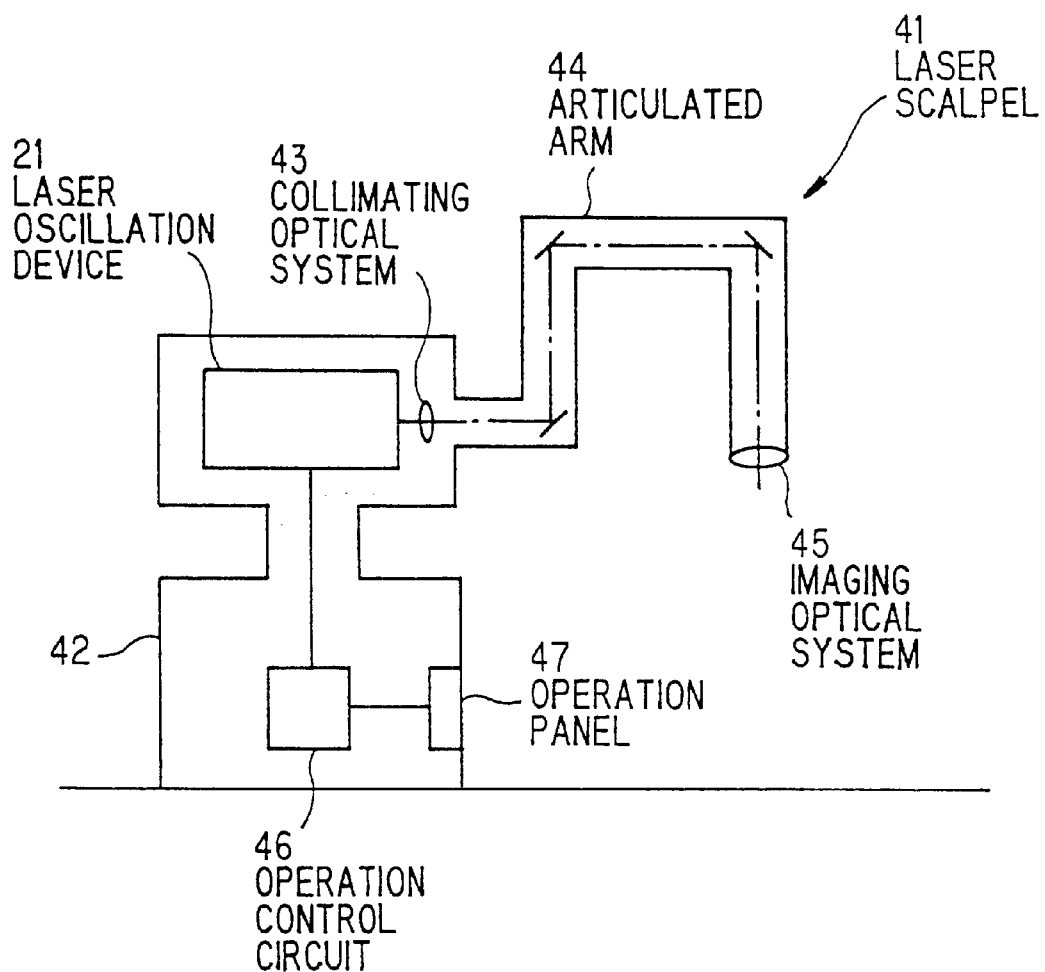
FIG. 4 is an illustration showing a laser scalpel 41 in a preferred embodiment according to the invention.
Figure 5:
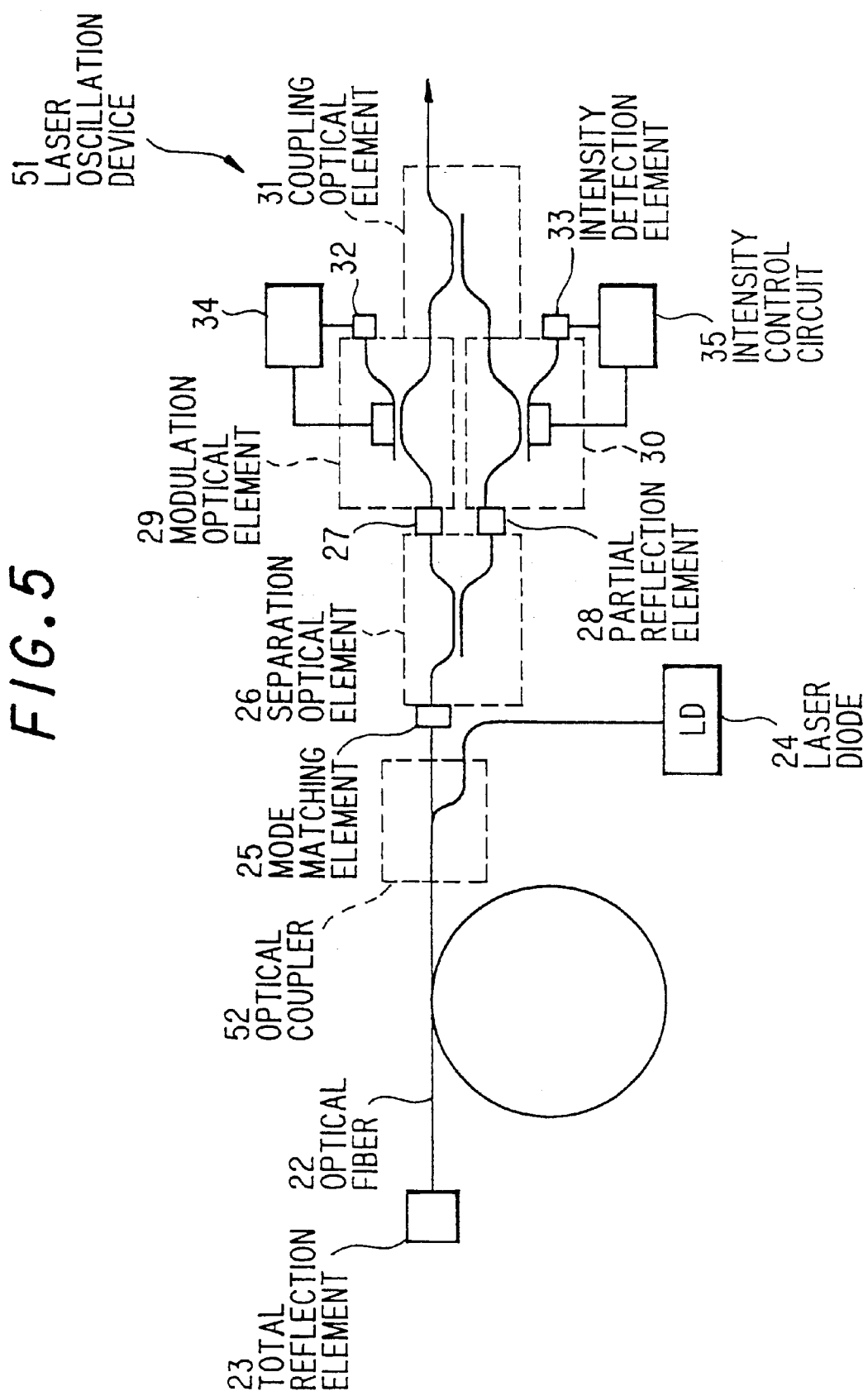
FIG. 5 is an illustration showing a modification of the laser oscillation device in FIG. 3.
Figure 6:
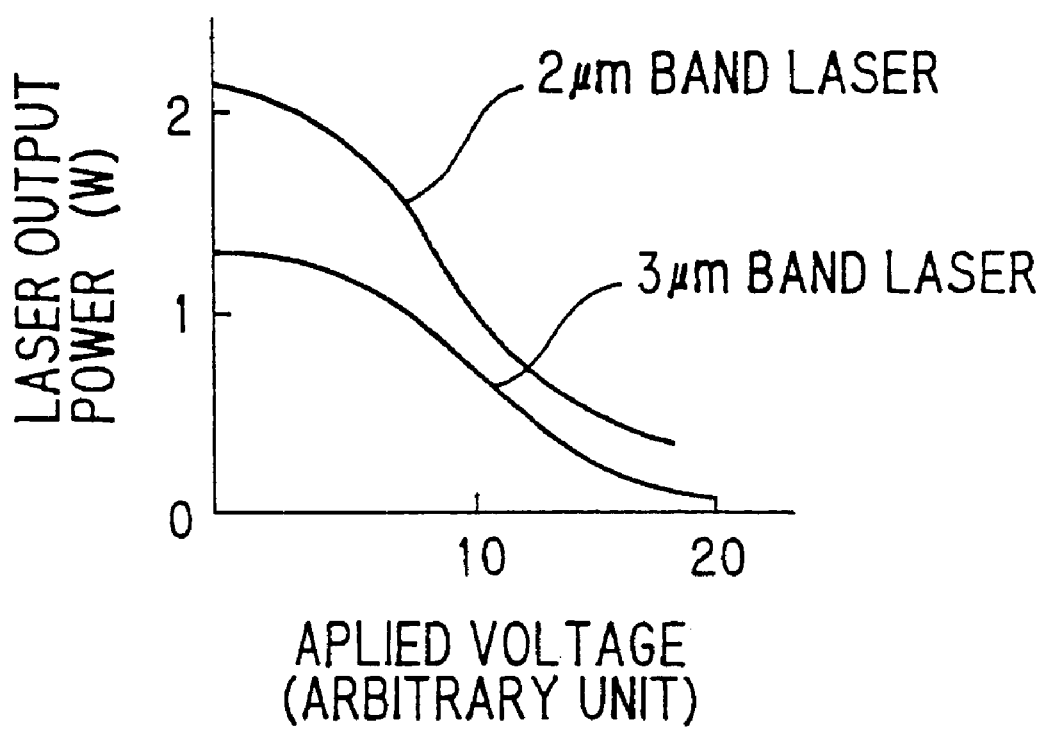
FIG. 6 is a characteristic diagram showing the relationship between voltage applied to optical coupler as a modulation optical means and intensity of laser beam for each of multiple wavelengths.

The preferred embodiments of the invention will be explained below, referring to the drawings. FIG. 3 is an illustration showing a laser oscillation device in the preferred embodiment of the invention, FIG. 4 is an illustration showing a laser scalpel in the preferred embodiment of the invention, FIG. 5 is an illustration showing a modification of the laser oscillation device of the above embodiment of the invention, and FIG. 6 is a characteristic diagram showing the relationship between voltage applied to optical coupler as modulation optical means and intensities of laser beam for multiple wavelengths.

Like the laser oscillation devices 1, 11, a laser oscillation device 21 of the embodiment is, as shown in FIG. 3, also equipped with an optical fiber 22, as a gain medium, with a core diameter of 10 $\mu$m and a total length of 2 m. The optical fiber 22 is of fluoride glass mainly including zirconium fluoride. To its core, about 0.25 wt % of holmium ion, rare-earth ion, as laser ion is doped.

To one end of the optical fiber 22, a total reflection element 23 as a total reflection means is connected. Through the total reflection element 23, a laser diode 24 as an excitation emission means is opposed thereto. The laser diode 24 emits light at a wavelength of about a 1.1 $\mu$m. By this emission, holmium ion of the optical fiber 22 is excited and one laser beam including wavelength components of 3 $\mu$m and 2 $\mu$m is generated in cascade oscillation.

The total reflection element 23 which is, for example, of a dichroic mirror efficiently transmits light beam with an excitation wavelength of about 1.1 $\mu$m but efficiently and uniformly reflects light beam with oscillation wavelengths of 3 $\mu$m and 2 $\mu$m resonated by the optical fiber 22.

Meanwhile, the basic structure and principle of the laser oscillation device 21 described above are detailed in Japanese patent application No. 09-146735 (1997) invented and applied commonly by inventor and applicant of this application. However, different from this application and prior arts, in the laser oscillation device 21 of this embodiment, one end of separation optical element 26 as a separation optical means is connected through a mode matching element 25 to another end of the optical fiber 22. To the other two ends of the separation optical element 26, two partial reflection elements 27, 28 as multiple partial reflection means are connected.

The mode matching element 25 is, for example, of a ball-type sapphire micro-lens, which helps match the mode field diameters of the optical fiber 22 and the separation optical element 26. The separation optical element 26 is composed of a plane waveguide type optical coupler, which is of lithium niobate, where as described earlier its one end is structured single-way and its another end is separated into two ways.

Thus, the separation optical element 26 separates one laser beam supplied from the optical fiber 22 into wavelength components of 3 $\mu$m and 2 $\mu$m, which are each supplied to the two partial reflection elements 27, 28. Laser beams of 3 μm and 2 μm wavelengths reflected separately by the partial reflection elements 27, 28 are coupled into one beam, feedbacked to the optical fiber 22.

The first partial reflection element 27 is composed of dielectric multilayer film, which it formed at the end face of the separation optical element 26, that reflects laser beam of 3 μm wavelength separated by the separation optical element 26 and transmits this laser beam according to the intensity. The second partial reflection element 28 is also composed of dielectric multilayer film, which is formed at the end face of the separation optical element 26, that reflects laser beam of 3 μm wavelength and transmits this laser beam according to the intensity.

In the laser oscillation device 21 of the embodiment, part continuing from the total reflection element 23 to the partial reflection elements 27, 28 corresponds to a so-called laser resonator. However, when laser beam is resonated by this laser resonator, the wavelengths of laser beam reflected by the two partial reflection elements 27, 28 are different as described above.

The two partial reflection elements 27, 28 each are formed to have such a refection factor that the resonance operation can be optimized for each of laser beams with two wavelengths. For example, the reflection factor of the first partial reflection element 27 to a wavelength component of 3 μm is 4%, and the reflection factor of the second partial reflection element 28 to a wavelength component of 2 μm is 2%.

Further, in the laser oscillation device 21 of this embodiment, one ends of two modulation optical elements 29, 30 as modulation optical means are connected respectively to the outer faces of the two partial reflection elements 27, 28. To other ends of the two modulation optical elements 29, 30, two ends of a coupling optical elements 31 as a coupling optical means are connected respectively.

Also, to the two modulation optical elements 29, 30, two intensity detection element 32, 33 as multiple intensity detection means are connected respectively. To the two intensity detection elements 32, 33, two intensity control circuits 34, 35 as multiple intensity control means are connected respectively.

The two modulation optical elements 29, 30 each are composed of a birefringent crystal waveguide type optical coupler, which is of lithium niobate, that generates Pockels effect as electro-optic effect. To the feeder terminals, the two intensity control circuits 34, 35 are feedback-connected respectively.

Thus, the transmissivities of the two modulation optical elements 29, 30 are varied respectively based on electro-optic effect by voltage applied from the two intensity control circuits 34, 35. Therefore, the intensities of laser beams with 3 μm and 2 μm wavelengths, which are separated by the separation optical element 26 and transmit through the two partial reflection elements 27, 28, are modulated separately.

The two intensity detection elements 32, 33 are, for example, composed of a photodiode, which detects the intensity of laser beam modulated by each of the two modulation optical elements 29, 30, outputting a detection signal. The two intensity control circuits 34, 35 are, for example, composed of a power-supply circuit connected with a microcomputer, which controls separately voltage applied to the modulation optical elements 29, 30 according to the detection result of the intensity detection elements 32, 33 and given control conditions.

The coupling optical element 31 is composed of a plane waveguide type two-way-separated optical coupler, which is of lithium niobate, that couples two laser beams with 3 μm and 2 μm wavelengths modulated separately by the two modulation optical elements 29, 30 into one beam, then outputting it from its end face.

The laser oscillation device 21 thus composed can be used as part of a laser scalpel 41, as shown in FIG. 4. In the laser scalpel 41 of this embodiment, the laser oscillation device 21 is fixed inside a main body 42, and a collimating optical system 43 is disposed on the emission optical axis of the laser oscillation device 21. On the transmission optical path of the collimating optical system 43, an articulated arm 44 as a laser leading means is disposed. To the tip portion of the articulated arm 44, an imaging optical system 45 as an imaging optical means is attached.

The collimating optical system 43 is composed of various lenses, converting laser beam emitted from the laser oscillation device 21 into parallel light beam. The articulated arm 44 has a structure that multiple hollow arms are sequentially linked movably by a joint mechanism, at the position of which polarizing mirrors are built in.

Thus, the articulated arm 44 supports the imaging optical system 45 on the tip portion movably, leading laser beam collimated by the collimating optical system 43 to the position of the imaging optical system 45. This imaging optical system 45 is also composed of various lenses, which converge collimated light beam on a given position.

Also, to the laser diode 24 and the intensity control circuit 34, 35 of the laser oscillation device 21, an operation control circuit 46 is connected. An operation panel 47 is connected to the operation control circuit 46. The operation control circuit 46 controls the operations of the laser diode 24 and the intensity control circuit 34, 35 of the laser oscillation device 21 according to the manual operation of the operation panel 47.

The laser oscillation method of the laser oscillation device 21 in the embodiment composed as above-mentioned is explained below. First, when the laser diode 24 emits light, this light is led through the total reflection element 23 to the optical fiber 22. Thereby, holmium ion doped into the optical fiber 22 is excited to generate one laser beam including 3 μm and 2 μm wavelength components.

This laser beam is, regardless of wavelength, reflected uniformly by the total reflection element 23, at one end of the optical fiber 22. But, at another end of the optical fiber 22, it is reflected separately by the two partial reflection elements 27, 28 after being separated by the separation optical element 26 into 3 μm and 2 μm wavelength components.

By these reflections, laser beam resonates and the 3 μm and 2 μm wavelength components each are led to the two modulation optical elements 29, 30 from the two partial reflection elements 27, 28. By the modulation optical elements 29, 30, the intensity of laser beams with 3 μm and 2 μm wavelengths is modulated separately. Two laser beams intensity-modulated are coupled into one beam by the imaging optical element 31, then emitted.

As described above, laser beam emitted from the laser oscillation device 21 is collimated by the collimating optical system 43 of the laser scalpel 41, then led through inside the articulated arm 44 to the tip portion, converged on a given position by the imaging optical system as on the tip portion. Since the tip portion of the articulated arm 44 can be moved to an arbitrary position by the manual operation of user, the laser scalpel 41 in this embodiment can perform the operation such as incision of patient's body using laser beam.

Meanwhile, by operating manually the operation panel 47 of the laser scalpel 41 if necessary, the user can control the operation of laser diode 24 in the laser oscillation device 21 to turn on/off the emission of laser beam. Also, by controlling the operation of two modulation optical elements 29, 30 separately, the intensity of 3 μm and 2 μm wavelength components of one laser beam can be modulated separately.

In the laser oscillation device 21 of the embodiment, holmium ion, rare-earth ion, as laser ion is doped to the optical fiber 22, to which light beam of about 1.1 μm wavelength from the laser diode 24 is led.

Therefore, laser beam including 3 μm and 2 μm wavelength components suitable for the work of the laser scalpel 41 can be generated. The laser scalpel 41 of this embodiment can perform various works using laser beam including suitable wavelength components.

Although the laser oscillation device 21 of the embodiment can emit one laser beam including 3 μm and 2 μm wavelength components as described above, in resonating this laser beam, one laser beam is divided into two wavelength components by the separation optical element 26, then reflected separately by the two partial reflection elements 27, 28.

Since the two partial reflection elements 27, 28 each are formed to have such a refection factor that the resonance operation can be optimized for each wavelength component of 3 μm or 2 μm as described earlier, the laser oscillation device 21 of the embodiment can resonate separately laser beams of 3 μm and 2 μm wavelengths in optimum conditions.

Moreover, as described earlier, laser beams of 3 μm and 2 μm wavelengths modulated separately by the two modulation optical elements 29, 30 are coupled into one beam by the coupling optical element 31, then emitted. Thus, one laser beam that wavelength components of 3 μm and 2 μm included are modulated separately can be emitted. Therefore it can function effectively as the laser beam source of the laser scalpel 41 requiring such laser beam.

Furthermore, since the laser oscillation device 21 of the embodiment modulates separately two laser beams divided for the respective wavelengths by the two modulation optical elements 29, 30, the intensity of two wavelength components included in one laser beam can be modulated as desired separately.

Especially, the intensities of laser beams of 3 μm and 2 μm wavelengths modulated separately by the two modulation optical elements 29, 30 are detected by the two intensity detection elements 32, 33, respectively. In response to the detection result of the two intensity detection elements 32, 33, the modulation operation of the two modulation optical elements 29, 30 is feedback controlled by the intensity control circuits 34, 35. Therefore, the intensity of laser beams with two wavelengths modulated separately can be kept in desired conditions accurately.

Further, since the transmissivity of the modulation optical elements 29, 30 changes based on electro-optic effect, the intensity of laser beams with two wavelengths can be controlled easily by the output voltage of the intensity control circuits 34, 35. Also, in the laser scalpel 41 of the embodiment, the operation of the intensity control circuits 34, 35 of the laser oscillation device 21 can be controlled by operating the operation panel 47 manually.

Therefore, the laser oscillation device 21 of the embodiment can function effectively as the laser beam source of the laser scalpel 41. The laser scalpel 41 of this embodiment can perform various works while controlling separately and accurately the intensity of two wavelength components included in one laser beam into desired conditions.

Also, in the laser oscillation device 21 of the embodiment, the separation optical element 26 is composed of a waveguide type optical coupler, therefore although optical loss to high-order transmission mode of the optical fiber 22 is large, optical loss to low-order transmission mode is so small and even with multiple wavelengths one laser beam can be transmitted at a good efficiency.

Further, since the mode field diameter between the optical fiber 22 and the separation optical element 26 is aligned by the mode matching element 25, laser beam can be transmitted from the optical fiber 22 to the separation optical element 26. In addition, since the respective elements 26, 29, 30 and 31 composed of a waveguide type optical coupler are of lithium niobate, they do not absorb laser beam of 3 μm and 2 μm wavelengths differently from silica glass. Also, since the optical fiber 22 is of fluoride glass, it does not absorb laser beam of 3 μm and 2 μm wavelengths.

Also, in the laser oscillation device 21 of the embodiment, the laser diode 24 is disposed at one end of the optical fiber 22 through the total reflection element 23. However, since light beam with an excitation wavelength generated from the laser diode 24 is transmitted through the total reflection element 23 to the optical fiber 22 at a high efficiency and light beam with oscillation wavelength generated at the optical fiber 22 is reflected by the total reflection element 23 to resonate at a high efficiency, laser beam can be excited and resonated properly with a simple structure.

Meanwhile, this invention is not limited to the above embodiment and can accept any modifications in the range of not exceeding the subject matter. For example, although in the above embodiment the laser oscillation device 21 is used as part of the laser scalpel 41, the laser oscillation device 21 of this invention can be used for other various apparatuses.

Further, for the laser scalpel 41 in the above embodiment, the laser leading means for leading movably laser beam emitted from the laser oscillation device 21 to a desired position is composed of the articulated arm 44. However, it can be composed of, for example, an optical fiber made of fluoride glass.

Also, the laser oscillation device 21 in the above embodiment emits one laser beam including two wavelength components of 3 μm and 2 μm taking the use for the laser scalpel 41 into account. However, wavelength included in laser beam and the number can be set arbitrarily according to application.

Further, although in the laser oscillation device 21 in the above embodiment the laser diode 24 is disposed at one end of the optical fiber 22 through the total reflection element 23, light emitted from the laser diode 24 can be led to axis part of the optical fiber 22 by a dedicated coupler 52, as shown in a laser oscillation device 51 in FIG. 5.

In the laser oscillation device 51, since light emitted from the laser diode 24 it led to axis part of the optical fiber 22, it is not necessary to lead light emitted from the laser diode 24 to the end of the optical fiber 22. Therefore, applying to the composition described above, the separation optical element 26 and the partial reflection elements 27, 28 can be disposed at both ends of the optical fiber 22. In this case, since two wavelength components of laser beam to be resonated can be reflected at both ends in optimum conditions, the laser resonation can be performed in more suitable operation conditions.

Also, in the above embodiment, the intensity of laser beam is modulated using the optical coupler whose transmissivity changes according to electro-optic effect as the modulation optical elements 29, 30. However, an optical coupler whose transmissivity changes according to thermo-optic effect can be also used as the modulation optical elements.

Further, although in the above embodiment holmium ion, rare-earth ion, as laser ion is doped to the optical fiber 22 to generate laser beam of 3 μm and 2 μm wavelengths, thulium or erbium ion can be also doped.

Although in the above embodiment light with an excitation wavelength of about 1.1 μm is generated by the laser diode 24 to generate laser beam of 3 μm and 2 μm wavelengths, the excitation wavelength of about 890 nm can be also employed. For this wavelength, various light sources can be used.

Although in the above embodiment the respective elements 26, 29, 30 and 31 composed of a waveguide type optical coupler are of lithium niobate to prevent laser beam of 3 μm and 2 μm wavelengths from being absorbed, they can be of lithium tantalate or barium citanate.

Although in the above embodiment the mode field diameter of the optical fiber 22 and the separation optical element 26 is aligned by the mode matching element 25 composed of micro-lenses, the mode aligning means can be also given by forming the end face of the optical fiber 22 into global.

When the laser oscillation device 21 is made actually with the respective elements 26, 29, 30 and 31 composed of an optical coupler of lithium niobate, it is confirmed that laser beam with wavelengths of 3 μm and 2 μm can be transmitted at a transmissivity of 99% or more. Also, when the optical fiber 22 with the end face formed global is junctioned to the separation optical element 26 as an optical coupler, it is confirmed that a coupling efficiency of 95% or more can be realized.

Furthermore, when the laser output of the laser diode 24 is 4 W, it is confirmed that the laser output for a wavelength component of 3 μm is 1.5 W and the laser output for a wavelength component of 2 μm is 2 W. Also, it is confirmed that by controlling voltage applied to the modulation optical elements 29, 30 the output power to wavelength components of 3 μm and 2 μm in one laser beam can be changed separately and arbitrarily as shown in FIG. 6.

Advantages of the Invention

In the first type of laser oscillation device of the invention, one laser beam including multiple wavelength components is emitted from at least one end of optical fiber, separated into multiple wavelength beams by the separation optical means. Each of multiple wavelength beams separated is reflected separately by each of multiple reflection means. Thus, laser beams to resonate are reflected by a reflection factor different to each of multiple wavelength components. Therefore, the operation condition in laser beam resonance can be optimized for each of multiple wavelength components.

In the second type of laser oscillation device of the invention, one laser beam including multiple wavelength components is generated by exciting the laser ion in the optical fiber by light emitted from the excitation emission means. Laser beam is reflected uniformly, regardless of wavelength, by the total reflection means at one end of optical fiber, but at another end of optical fiber laser beam is separated into multiple wavelength components by the separation optical means, then reflected separately by the multiple partial reflection means. Thus, laser beams to resonate are reflected by a reflection factor different to each of multiple wavelength components. Therefore, the operation condition in laser beam resonance can be optimized for each of multiple wavelength components.

Also, in the second type of laser oscillation device, light beam with an excitation wavelength generated from the excitation emission means is transmitted through the total reflection means at a high efficiency, led to the optical fiber. Light beam with an oscillation wavelength generated by the optical fiber is reflected by the total reflection means at a high efficiency to resonate. Thus, laser beam can be excited and resonated efficiently, with the simple structure.

In the third type of laser oscillation device of the invention one laser beam including multiple wavelength components is generated by exciting the laser ion in the optical fiber by light emitted from the excitation emission mean. Laser beam is separated into multiple wavelength components by the separation optical means at both ends of optical fiber, then reflected separately by the multiple partial reflection means. Thus, laser beams to resonate are reflected by a reflection factor different to each of multiple wavelength components. Therefore, the operation condition in laser beam resonance can be optimized for each of multiple wavelength components.

Although the invention has been described with respect to specific embodiment for complete and clear disclosure, the appended claims are not to be thus limited but are to be construed as embodying all modification and alternative constructions that may be occurred to one skilled in the art which fairly fall within the basic teaching here is set forth.

What is claimed is:

1. A method for separately reflecting individual wavelength components of a laser beam having a plurality of wavelength components, comprising the steps of:

providing an optical fiber having a core doped with a laser ion;

exciting the laser ion and generating one laser beam having multiple wavelength components;

separating said laser beam emitted from at least one end of said optical fiber into a plurality of beams having multiple wavelengths;

reflecting uniformly the one laser beam at a first end of the optical fiber;

aligning a mode field diameter of the optical fiber with a separation optical element;

separating the one laser beam emitted from a second end of the optical fiber, into a plurality of laser beams each having a distinct wavelength; and reflecting separately each beam of said plurality of beams.

2. A device for separately reflecting individual wavelength components of a laser beam having a plurality of wavelength components, comprising:

an optical fiber having a doped laser ion;

a first reflection element for reflecting said laser beam at a first end of said optical fiber;

a second reflection element for reflecting said laser beam at a second end of said optical fiber;

an excitation emission means for generating light, said light exciting the laser ion;

a separation optical means being at least at one end of said optical fiber and separating said laser beam into a plurality of beams each having a distinct wavelength; and mode matching element, between said optical fiber and said separation optical means, for aligning a mode field of said optical fiber and said separation optical means;

said plurality of beams being separately reflected by said first and second reflection elements.

3. A device for separately reflecting individual wavelength components of a laser beam having a plurality of wavelength components, comprising:

optical fiber having a doped laser ion;

an excitation emission means for generating a laser beam having multiple wavelength components by exciting the laser ion in the optical fiber by light emission;

a total reflection means being at a first end of said optical fiber and uniformly reflecting said laser beam;

a separation optical means being at a second end of said optical fiber and separating said laser beam into a plurality of beams each having a distinct wavelength; and a plurality of partial reflection means for separately reflecting each said plurality of laser beams.

4. The device, according to claim 3, wherein:

said total reflection means transmitting said laser beam with an excitation wavelength generated from said excitation emission means, and reflecting said laser beam with an oscillation wavelength resonated by said optical fiber; and said excitation emission means opposing said first end of said optical fiber through said total reflection means.

5. The device according to claim 3, wherein the light emitted from said excitation emission means is directed to an axis part of said optical fiber.

6. The device according to claim 3, wherein said separation optical means comprising a waveguide optical coupler.

7. The device according to claim 3, wherein said separation optical means comprising a waveguide optical coupler that is of a material that does not absorb 3 $\mu$m and 2 $\mu$m wavelengths.

8. The device according to claim 3, further comprising a mode matching means for aligning a mode field diameter of said optical fiber and said separation optical means.

9. The device according to claim 3, further comprising a plurality of modulation optical means for separately modulating said plurality of laser beams.

10. The device according to claim 9, wherein said modulation optical means comprising a waveguide optical coupler having a transmissivity that varies according to the electro-optic effect, by changing a voltage applied from an outside source.

11. The device according to claim 9, wherein said modulation optical means comprising a waveguide optical coupler having a transmissivity that varies according to the thermo-optic effect, by changing an electric power supplied from an outside source.

12. The device according to claim 9, wherein said modulation optical means comprising a waveguide optical coupler that is of a material that does not absorb 3 $\mu$m and 2 $\mu$m wavelengths.

13. The device according to claim 9, further comprising:

a plurality of intensity detection means for detecting an intensity of said plurality of laser beams; and an intensity control means for feedback controlling the modulation operation of said plurality of modulation optical means in response to a detection result of said plurality of intensity detection means.

14. The device according to claim 3, wherein said laser ion doped into said optical fiber is a rare-earth ion.

15. The device according to claim 3, wherein said laser ion doped into said optical fiber is a holmium ion.

16. The device according to claim 3, wherein said excitation emission means emits light at a wavelength of about 890 nm or about 1.1 $\mu$m.

17. A device for separately reflecting individual wavelength components of a laser beam having a plurality of wavelength components, comprising:

an optical fiber having a doped laser ion;

an excitation emission means for generating a laser beam including multiple wavelength components by exciting the laser ion by light emission;

a pair of separation optical means located individually at both ends of said optical fiber and separating said laser beam into a plurality of beams each having a distinct wavelength; and a plurality of partial reflection means for separately reflecting each said plurality of laser beams.

18. The device according to claim 17, wherein the light emitted from said excitation emission means is directed to an axis part of said optical fiber.

19. The device according to claim 17, wherein said separation optical means comprising a waveguide optical coupler.

20. The device according to claim 17, wherein said separation optical means comprising a waveguide optical coupler that is of a material that does not absorb 3 $\mu$m and 2 $\mu$m wavelengths.

21. The device according to claim 17, further comprising a mode matching means for aligning a mode field diameter of said optical fiber and said separation optical means.

22. The device according to claim 17, further comprising a plurality of modulation optical means for separately modulating said plurality of laser beams.

23. The device according to claim 22, wherein said modulation optical means comprising a waveguide optical coupler having a transmissivity that varies according to the electro-optic effect, by changing a voltage applied from an outside source.

24. The device according to claim 22, wherein said modulation optical means comprising a waveguide optical coupler having a transmissivity that varies according to the thermo-optic effect, by changing an electric power supplied from an outside source.

25. The device according to claim 22, wherein said modulation optical means is composed of a waveguide optical coupler that is of a material that does not absorb 3 $\mu$m and 2 $\mu$m wavelengths.

26. The device according to claim 22, further comprising:

a plurality of intensity detection means for detecting an intensity of said plurality of laser beams; and an intensity control means for feedback-controlling the modulation operation of said plurality of modulation optical means in response to a detection result of said plurality of intensity detection means.

27. The device according to claim 26, wherein said coupling optical means is composed of a waveguide optical coupler that is of a material that does not absorb 3 $\mu$m and 2 $\mu$m wavelengths.

28. The device according to claim 22, further comprising a coupling optical means for coupling said plurality of laser beams into one beam.

29. The device according to claim 28, wherein said coupling optical means comprising a waveguide optical coupler that is of a material that does not absorb 3 $\mu$m and 2 $\mu$m wavelengths.

30. The device according to claim 17, wherein said laser ion doped into said optical fiber is a rare-earth ion.

31. The device according to claim 17, wherein said laser ion doped into said optical fiber is a holmium ion.

32. The device according to claim 17, wherein said excitation emission means emits light at a wavelength of about 890 nm or about 1.1 $\mu$m.

33. The device according to claim 17, further comprising a coupling optical means for coupling said plurality of laser beams into one beam.

34. A laser scalpel comprising:

said device defined in claim 27;

an articulatable laser leading means for leading said laser beam output from said laser oscillation device to a tip portion of said laser leading means; and an imaging optical means located near said tip portion for converging said laser beam.

35. A laser scalpel comprising:

a device for separately reflecting individual wavelength components of a laser beam having a plurality of wavelength components, comprising an optical fiber having a doped laser ion;

an excitation emission means for generating a laser beam including multiple wavelength components by exciting the laser ion by light emission;

a pair of separation optical means located individually at both ends of said optical fiber and separating said laser beam into a plurality of beams each having a distinct wavelength;

a plurality of partial reflection means for separately reflecting each said plurality of laser beams;

a plurality of modulation optical means for separately modulating said plurality of laser beams; and a coupling optical means for coupling said plurality of laser beams into one beam, said coupling optical means comprising a waveguide optical coupler that is of a material that does not absorb 3 $\mu$m and 2 $\mu$m wavelengths;

an articulatable laser leading means for leading said laser beam output from said laser oscillation device to a tip portion of said laser leading means; and an imaging optical means adjacent said tip portion for converging said laser beam.

* * * * *